US011253627B2

(12) United States Patent
Bito et al.

(10) Patent No.: US 11,253,627 B2
(45) Date of Patent: Feb. 22, 2022

(54) EMBOLIC MATERIAL AND METHOD FOR PRODUCING SAME

(71) Applicant: DREAM MEDICAL PARTNERS CORPORATION, Tokyo (JP)

(72) Inventors: Kenta Bito, Yokohama (JP); Terumitsu Hasebe, Hachioji (JP); Atsushi Hotta, Yokohama (JP)

(73) Assignee: DREAM MEDICAL PARTNERS CORPORATION, Tokyo (JP)

(*) Notice: Subject to any disclaimer, the term of this patent is extended or adjusted under 35 U.S.C. 154(b) by 252 days.

(21) Appl. No.: 16/485,955

(22) PCT Filed: Feb. 15, 2018

(86) PCT No.: PCT/JP2018/005264
§ 371 (c)(1),
(2) Date: Oct. 31, 2019

(87) PCT Pub. No.: WO2018/151214
PCT Pub. Date: Aug. 23, 2018

(65) Prior Publication Data
US 2020/0054783 A1 Feb. 20, 2020

(30) Foreign Application Priority Data
Feb. 15, 2017 (JP) .................... 2017-026126

(51) Int. Cl.
*A61K 9/16* (2006.01)
*A61L 24/00* (2006.01)
*A61K 31/282* (2006.01)
*A61K 47/34* (2017.01)
*A61K 49/04* (2006.01)
*A61L 24/04* (2006.01)

(52) U.S. Cl.
CPC ........ *A61L 24/0089* (2013.01); *A61K 31/282* (2013.01); *A61K 47/34* (2013.01); *A61K 49/0414* (2013.01); *A61K 49/0442* (2013.01); *A61L 24/0005* (2013.01); *A61L 24/0015* (2013.01); *A61L 24/046* (2013.01); *A61L 2300/224* (2013.01); *A61L 2300/30* (2013.01)

(58) Field of Classification Search
CPC ...... A61K 9/16; A61K 9/1605; A61K 9/1611; A61K 9/1617; A61K 9/1629; A61K 9/1647; A61K 9/1682
See application file for complete search history.

(56) References Cited

U.S. PATENT DOCUMENTS

| | | | |
|---|---|---|---|
| 2004/0241094 A1 | 12/2004 | Chung et al. | |
| 2010/0041744 A1 | 2/2010 | Chung et al. | |
| 2011/0212179 A1 | 9/2011 | Liu | |
| 2012/0270295 A1 | 10/2012 | Choo et al. | |
| 2013/0022545 A1 | 1/2013 | Lee et al. | |
| 2013/0287697 A1* | 10/2013 | Lin | A61L 24/04 424/9.4 |
| 2013/0295020 A1 | 11/2013 | Abraham et al. | |
| 2014/0212355 A1 | 7/2014 | Trollsas et al. | |
| 2016/0030602 A1 | 2/2016 | Dreher et al. | |
| 2016/0199378 A1 | 7/2016 | Niichel | |

FOREIGN PATENT DOCUMENTS

| | | |
|---|---|---|
| JP | H05969 A | 1/1993 |
| JP | 2004175698 A | 6/2004 |
| JP | 2004313759 A | 11/2004 |
| JP | 2005504070 A | 2/2005 |
| JP | 2012-507562 A | 3/2012 |
| JP | 2013512660 A | 4/2013 |
| JP | 2014508701 A | 4/2014 |
| JP | 2016508486 A | 3/2016 |
| JP | 2016084298 A | 5/2016 |
| JP | 2016515158 A | 5/2016 |
| WO | 2015036626 A1 | 3/2015 |
| WO | 2016114812 A1 | 7/2016 |

OTHER PUBLICATIONS

Extended European Search Report dated Nov. 27, 2020 in the corresponding European Patent Application No. 18753904.4.
Choi Jin Woo et al.,"Doxorubicin-loaded poly(lactic-co-glycolic acid) microspheres prepared using the solid-in-oil-in-water method for the transarterial chemoembolization of a liver tumor", Colloids and Surface B: Biointerfaces, 2015, vol. 132, pp. 305-312.
Office Action dated Jan. 5, 2021 in the corresponding Japanese Patent Application No. 2017-026126 and its full machine English translation.
International Search Report for corresponding PCT International Application No. PCT/JP2018/005264, PCT/ISA/210, dated May 1, 2018.
Written Opinion of the International Searching Authority for corresponding PCT International Application No. PCT/JP2018/005264, PCT/ISA/237 (in Japanese language), dated May 1, 2018.
Chen B. et al., "Experimental research of rabbit renal artery embolism with lipiodol-polylactic acid microspheres," Chin J Interv Imaging Ther, 2015, vol. 12, No. 8, pp. 503-507, English abstract.
International Preliminary Report on Patentability with translation of the Written Opinion of the International Searching Authority, International Application No. PCT/JP2018/005264, dated Aug. 20, 2019 (FormPCT/IB/338; Form PCT/IB/373; and Form PCT/ISA/237).
Office Action issued in the corresponding Japanese Patent Application No. 2017-026126, dated Mar. 30, 2021, and its machine English translation.

* cited by examiner

*Primary Examiner* — Micah Paul Young
(74) *Attorney, Agent, or Firm* — Renner, Otto, Boisselle & Sklar, LLP

(57) ABSTRACT

An embolic material contains at least one type of polymer and a liposoluble contrast medium. A method for producing an embolic material includes extruding a raw material that is in a molten state into a solvent, and cooling the raw material so as to solidify the raw material. The raw material contains a polymer and a liposoluble contrast medium.

3 Claims, 4 Drawing Sheets

EMBOLIC MATERIAL AND METHOD FOR PRODUCING SAME

CROSS-REFERENCE TO RELATED APPLICATION

This international application claims the benefit of Japanese Patent Application No. 2017-26126 filed on Feb. 15, 2017 with the Japan Patent Office, the entire disclosure of Japanese Patent Application No. 2017-26126 is incorporated in this international application by reference.

TECHNICAL FIELD

The present disclosure relates to an embolic material and a method for producing the same.

BACKGROUND ART

Known as a method for treating hepatocellular carcinoma is transcatheter arterial chemoembolization. In the transcatheter arterial chemoembolization, a part of a hepatic artery in vicinity of a tumor is blocked by an embolic material (See Patent Document 1).

PRIOR ART DOCUMENTS

Patent Documents

Patent Document 1: Japanese Unexamined Patent Application
Publication No. 2004-313759

SUMMARY OF THE INVENTION

Problems to be Solved by the Invention

Conventional embolic materials did not have sufficient visibility under X-ray fluoroscopy. Thus, identifying the positions where the embolic materials are present has been difficult. It is desirable that one aspect of the present disclosure provides an embolic material with high visibility under X-ray fluoroscopy and a method for producing such embolic material.

Means for Solving the Problems

One aspect of the present disclosure provides an embolic material comprising at least one type of polymer and a liposoluble contrast medium. Since the embolic material according to one aspect of the present disclosure contains the liposoluble contrast medium, visibility under X-ray fluoroscopy is high.

Another aspect of the present disclosure provides a method for producing an embolic material. The method comprises: extruding a raw material containing at least one type of polymer and a liposoluble contrast medium into a solvent, and being in a molten state; and cooling the raw material so as to solidify the raw material. Since the embolic material produced through the method for producing an embolic material according to another aspect of the present disclosure contains the liposoluble contrast medium, the visibility under the X-ray fluoroscopy is high. Moreover, the embolic material produced through the method for producing an embolic material according to another aspect of the present disclosure has a high uniformity in particle diameter.

EXPLANATION OF REFERENCE NUMERALS

Figure 1:
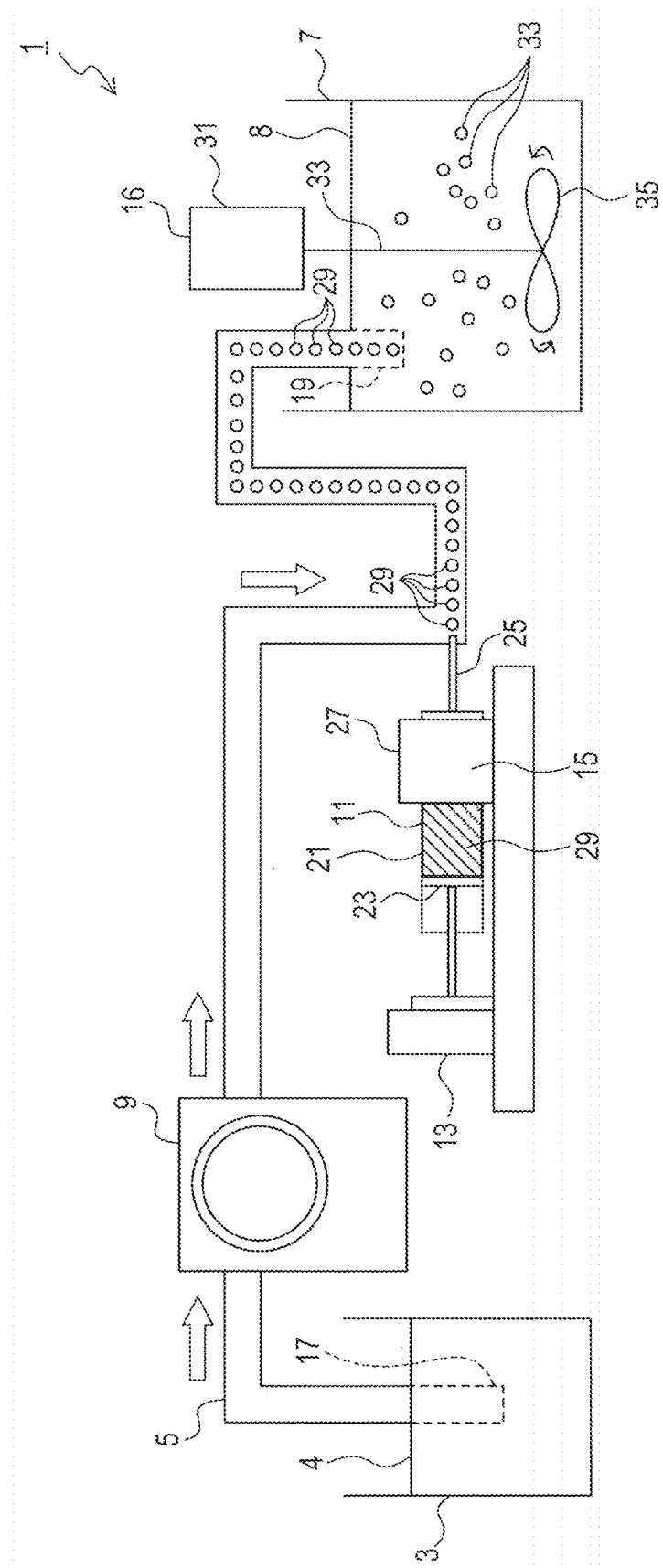
FIG. 1 is an explanatory diagram showing a structure of production apparatus.

1 . . . production apparatus, 3 . . . warm water tank, 4 . . . warm water, 5 . . . pipe, 7 . . . cold water tank, 8 . . . cold water, 9 . . . roller pump, 11 . . . syringe, 13 . . . syringe pump, 15 . . . heater, 16 . . . mixer, 17 . . . inlet, 19 . . . outlet, 21 . . . injection cylinder, 23 . . . plunger, 25 . . . injection needle, 27 . . . metal member, 29 . . . raw material, 33 . . . embolic material

MODE FOR CARRYING OUT THE INVENTION

Example embodiments of the present disclosure will be described with reference to the drawings.

1. Embolic Material

An embolic material comprises at least one type of polymer. The polymer is preferably biodegradable. If the polymer is biodegradable, complications in normal tissue deriving from the embolic material can be reduced. Moreover, if the polymer is biodegradable, it allows repeated usage of the embolic material to the same subject.

Examples of the biodegradable polymer include one or more selected from a group consisting of polycaprolactone, polylactate, a copolymer of polycaprolactone and polylactate, a mixture of polycaprolactone and polylactate, and a compound of polycaprolactone and polylactate. The polymer may be a mixture of two or more types of polymers. When the total mass of the polymer and a liposoluble contrast medium is 100 parts mass, the mass of the polymer is preferably within a range of 40 to 60 parts mass. If the mass of the polymer is within this range, the viscosity of the raw material tends to be at a suitable value in a method for producing the embolic material, which will be described below, facilitating the production of the embolic material.

The polymer is preferably a hydrophobic polymer. Use of the hydrophobic polymer facilitates mixing of the polymer and the liposoluble contrast medium. Examples of the hydrophobic polymer include polycaprolactone and polylactate.

If the embolic material further contains a pharmaceutical drug dissolved in the liposoluble contrast medium, the melting point of the polymer is preferably lower than a temperature at which the pharmaceutical drug is deactivated. If the melting point of the polymer is lower than the deactivation temperature, the raw material can be melted without deactivating the pharmaceutical drug in the production method to be described below. Moreover, if the melting point of the polymer is low, a temperature for heating the polymer can be set low, which in turn facilitates molding of the embolic material.

The embolic material comprises the liposoluble contrast medium. Since the embolic material comprises the liposoluble contrast medium, the visibility under X-ray fluoroscopy is high. The visibility under X-ray fluoroscopy is maintained even when the embolic material is in a partly degraded state, for example.

The liposoluble contrast medium is preferably swelled at a molecule level in a polymer network. Examples of the liposoluble contrast medium include ethyl ester of iodinated poppy-seed oil fatty acid. Examples of commercially available ethyl ester of iodinated poppy-seed oil fatty acid include Lipiodol (Registered Trademark). The liposoluble contrast medium may be other substances than ethyl ester of iodinated poppy-seed oil fatty acid. The liposoluble contrast medium is preferably a medium that can contain the pharmaceutical drug. The liposoluble contrast medium is preferably a medium that can dissolve the pharmaceutical drug. Examples of the pharmaceutical drug contained in the liposoluble contrast medium include those to be described below.

The embolic material may further comprise the pharmaceutical drug dissolved in the liposoluble contrast medium. If the embolic material further comprises the pharmaceutical drug, the embolic material demonstrates drug time-release properties. Examples of the pharmaceutical drug include an anticancer drug. Examples of the anticancer drug include miriplatin hydrate for injection. Examples of commercially available miriplatin hydrate for injection include MIRI-PLA™.

The embolic material can be used, for example, in a transcatheter arterial chemoembolization (TACE) intended for treating hepatocellular carcinoma. If the embolic material comprises the pharmaceutical drug, the embolic material can be used, for example, as drug-eluting beads (DEB) in the TACE. The embolic material can block, for example, a hepatic artery.

2. Method for Producing Embolic Material

In the method for producing an embolic material according to the present disclosure, a raw material comprising the at least one type of polymer and the liposoluble contrast medium and being in a molten state is extruded into a solvent, and the raw material is cooled and solidified.

As the polymer and the liposoluble contrast medium contained in the raw material, those described in the section "1. Embolic Material" can be used. The raw material may further comprise the pharmaceutical drug dissolved in the liposoluble contrast medium. As the pharmaceutical drug, those described in the section "1. Embolic Material" can be used.

As the solvent, water may be used, for example. As the means to extrude the raw material into the solvent, a syringe and a nozzle, for example, may be used. The diameters of openings of the syringe, the nozzle, and the like are preferably within a range of 0.01 to 0.9 mm. The particle diameters of the embolic material to be produced can be varied by adjusting the diameters of the openings.

The form of the raw material extruded into the solvent may be, for example, spherical shapes. The temperature of a part of the solvent into which the raw material is extruded may be, for example, comparable with the temperature of the raw material. For example, a part of the solvent into which at least the raw material is extruded flows in a given direction inside a pipe. A flow rate of the solvent flowing in the given direction is preferably within a range of 200 to 500 mL/min. The inner diameter of the pipe is preferably within a rage of 0.1 to 3 mm.

Examples of a way to cool the raw material include a way to pour the raw material together with the solvent into a container holding a coolant. The coolant may be, for example, the same substance as the solvent and have a temperature lower than that of the solvent. The coolant may be any of solid, liquid, and gas. Other publically known ways for cooling may be suitably selected and used.

The embolic material produced through the method for producing an embolic material according to the present disclosure is high in uniformity of the particle diameters. Moreover, due to the high uniformity in particle diameter, a process to sieve the embolic material so as to even out the particle diameters is dispensable. This eliminates or reduces damages to be caused to the embolic material in the sieving process.

EMBODIMENTS (1) Preparation of Raw Material 10 g of polycaprolactone and 10 g of Lipiodol were poured into a flask. A stir bar of a magnetic stirrer was also put into the flask. A nitrogen atmosphere was created in the flask. Providing the nitrogen atmosphere in the flask can inhibit oxidation of Lipiodol.

Subsequently, the flask was heated by a water bath at 80° C. While the flask was heated, the stir bar was rotated at 50 rpm. As a result, the raw material in the molten state comprising the polycaprolactone and Lipiodol and being was obtained.

(2) Structure of Production Apparatus 1

The structure of production apparatus 1 used for producing the embolic material will be described based on FIG. 1. The production apparatus 1 comprises a warm water tank 3, a pipe 5, a cold water tank 7, a roller pump 9, a syringe 11, a syringe pump 13, a heater 15, and a mixer 16.

The warm water tank 3 reserves warm water 4. The pipe 5 is a continuous pipe having an inner diameter of 3 mm. An inlet 17 of the pipe 5 is disposed in the warm water 4 reserved in the warm water tank 3. An outlet 19 of the pipe 5 is disposed in cold water 8 reserved in the cold water tank 7. The roller pump 9 is attached to the pipe 5 between the inlet 17 and the outlet 19. The roller pump 9 draws the warm water 4 in the warm water tank 3 from the inlet 17 and feeds the warm water 4 into the pipe 5. The warm water 4 that has flown inside the pipe 5 is discharged from the outlet 19 and enters the cold water tank 7.

The cold water tank 7 reserves the cold water 8. The syringe 11 comprises an injection cylinder 21, a plunger 23, and an injection needle 25. The injection needle 25 is inserted into the pipe 5 between the roller pump 9 and the outlet 19. The inner diameter of the injection needle 25 is from 0.05 to 0.8 mm. The syringe pump 13 pushes the plunger 23 into the direction of the injection needle 25. The heater 15 comprises a metal member 27, externally fitted to the injection cylinder 21, and a heat source, which is not shown, for heating the metal member 27.

The mixer 16 comprises a main body 31 incorporating a driving source which is not shown, a rotation shaft 33 downwardly extending from the main body 31, and a rotation blade 35 attached to the bottom end of the rotation shaft 33. Part of the rotation shaft 33 and the rotation blade 35 are disposed in the cold water 8 reserved in the cold water tank 7. The mixer 16 can rotate the rotation shaft 33 and the rotation blade 35 with the aforementioned driving source. When the rotation shaft 33 and the rotation blade 35 are rotated, the cold water 8 reserved in the cold water tank 7 is mixed.

(3) Production of Embolic Material

With the raw material prepared in the above-described (1) and the production apparatus 1, the embolic material was produced as follows. In the warm water tank 3, the warm water 4 at 80° C. was reserved. The temperature of the warm water 4 was also maintained at 80° C. in processing to be described below. The warm water 4 corresponds to the solvent. In the cold water tank 7, on the other hand, the cold water 8 at 0° C. was reserved. The temperature of the cold water 8 was also maintained at 0° C. in the processing to be described below. The cold water 8 in the cold water tank 7 was continuously mixed by the mixer 16.

Next, the roller pump 9 was driven to maintain a state in which the warm water 4 flows from the warm water tank 3 to the cold water tank 7 through the pipe 5. The temperature of the warm water 4 was 80° C. throughout the pipe 5. The flow rate of the warm water 4 was maintained at a constant value. The value of the flow rate was determined to be within a range of 200 to 500 mL/min.

Subsequently, the syringe 11 was filled with the raw material 29 produced in the above-described (1). Moreover, the temperature of the raw material 29 filled in the syringe 11 was maintained at 80° C. with the heater 15. The raw material 29 filled in the syringe 11 was thus always kept in the molten state.

Then, the plunger 23 was pushed in by the syringe pump 13 so as to eject the raw material 29 from the tip of the injection cylinder 21 into the pipe 5. As shown in FIG. 1, the ejected raw material 29 was separated into multiple particles. The form of the multiple particles was spherical shapes. The particulate raw material 29 flowed in the pipe 5 together with the warm water 4 and entered the cold water tank 7. The particulate raw material 29 was cooled in the cold water tank 7 and solidified so as to produce an embolic material 33. The form of particles of the embolic material 33 was spherical shapes.

(4) Calculation of Particle Diameter Distribution

Figure 2:
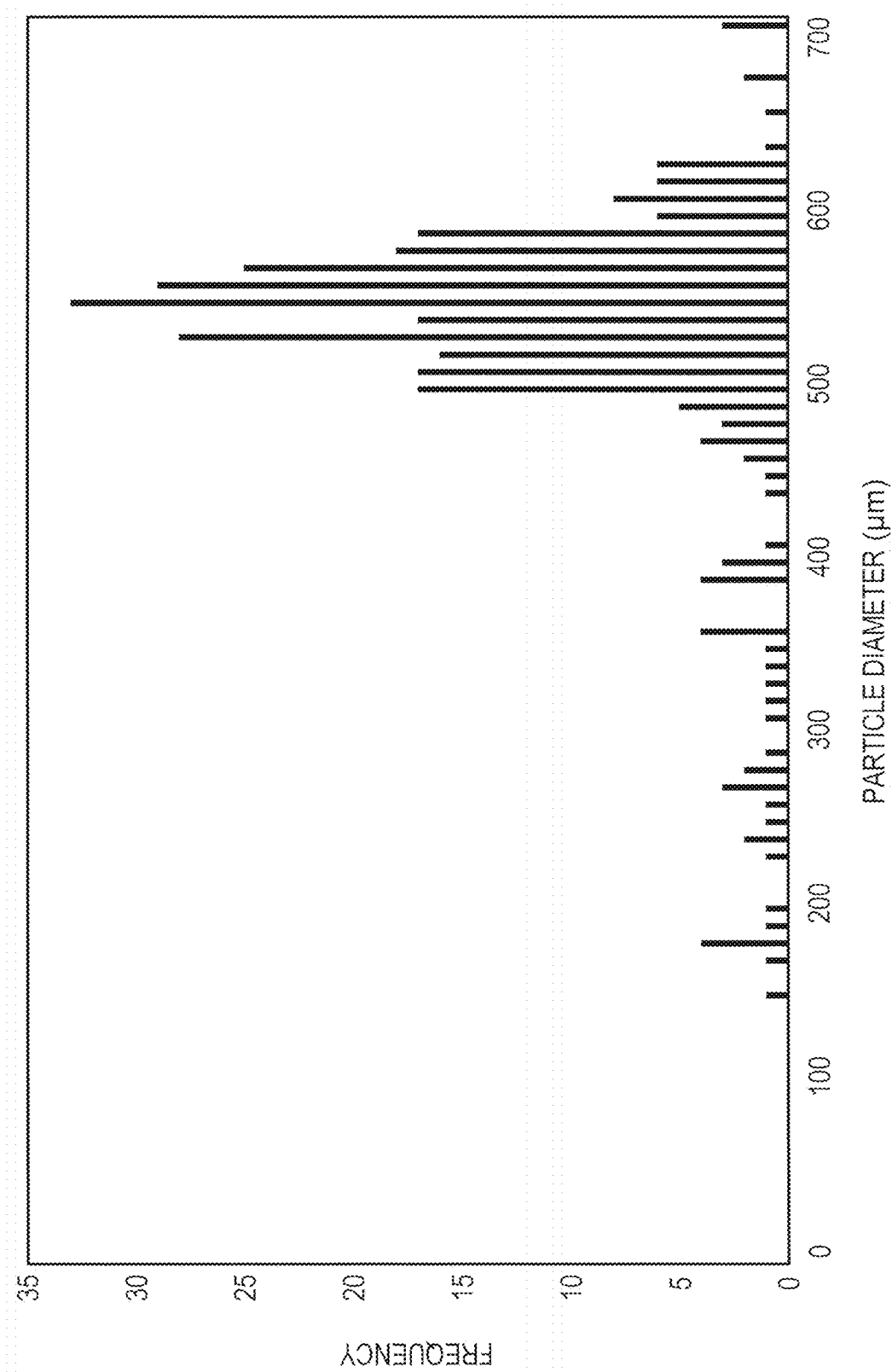
FIG. 2 is a graph showing a particle diameter distribution of an embolic material.

The particle diameter distribution of the embolic material produced in the above-described (3) was calculated. The method thereof is as follows. First, a photograph of the aggregate embolic material was taken with an optical microscope. In the photograph, the diameters of individual particles of the embolic material were measured with a software. Based on the measurement results, the particle diameter distribution was calculated. The calculated particle diameter distribution is shown in FIG. 2. The average particle diameter of the embolic material was 527 µm. As shown in FIG. 2, the particle diameter distribution of the embolic material was narrow. In other words, the uniformity of the embolic material in particle diameter was high.

(5) Evaluation for X-Ray Opacity

Figure 3:
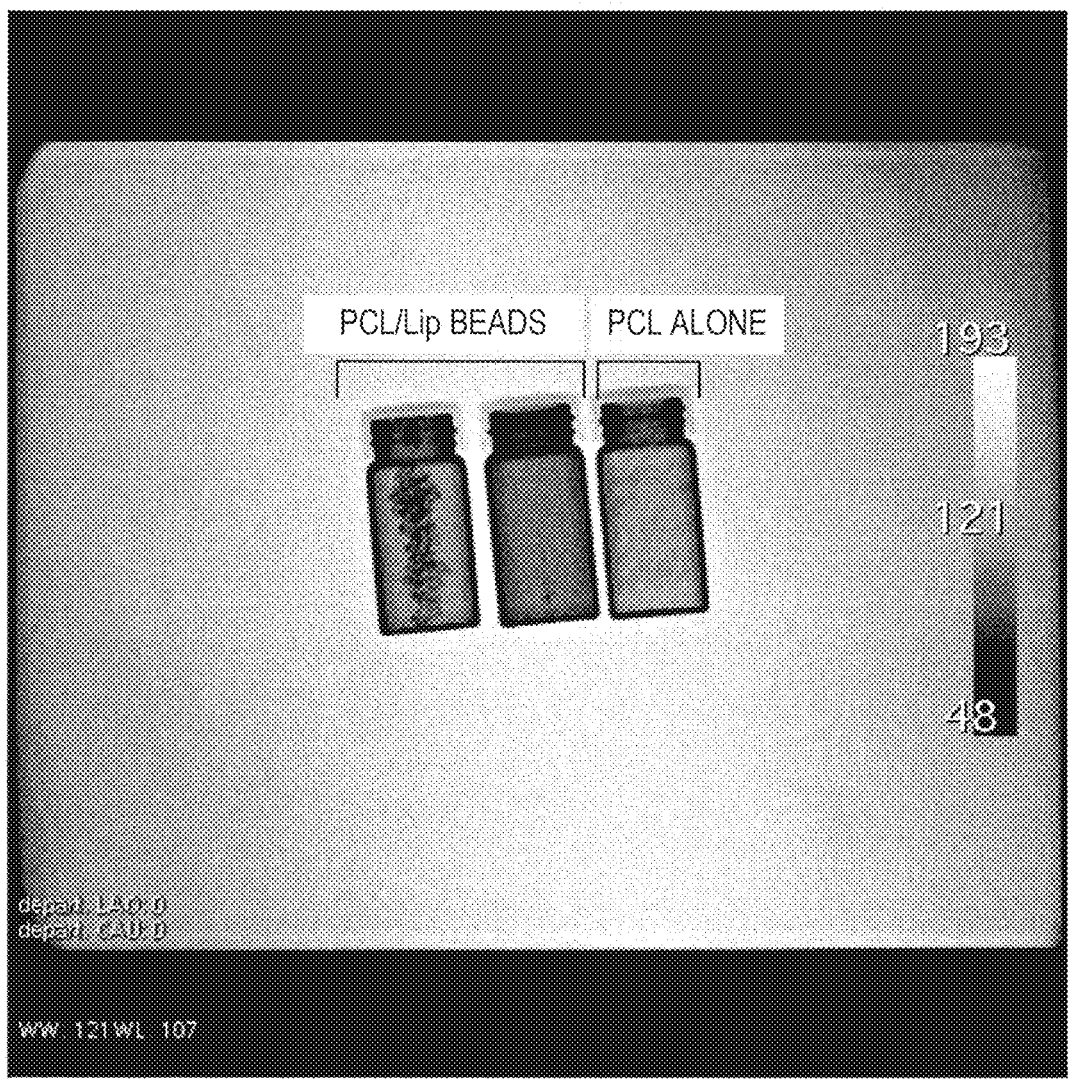
FIG. 3 is an X-ray fluoroscopic image acquired by capturing an image of sample bottles with embolic materials using an X-ray fluoroscopic device.

X-ray opacity of the embolic material produced in the above-described (3) was evaluated. The method thereof is as follows. The embolic material produced in the above-described (3) and water were poured into sample bottles. An image of the sample bottles was captured by the X-ray fluoroscopic device. FIG. 3 is an X-ray fluoroscopic image acquired by the capturing. "PCL/Lip BEADS" in FIG. 3 are the sample bottles with the embolic material produced in the above-described (3). In the sample bottles "PCL/Lip BEADS", the embolic material was shown in black.

"PCL ALONE" in FIG. 3 is a bottle with an embolic material of a comparative example. The embolic material of the comparative example was produced through a method which is basically the same as that in the above-described (3), but a raw material consisting only of polycaprolactone was used therein. In the sample bottle "PCL ALONE", the embolic material was shown with almost the same brightness as that of the background.

(6) Evaluation for Pharmaceutical Drug Time-Release Property (6-1) Preparation of Embolic Material for Evaluation 70 mg of MIRIPLA was dissolved in 4.3 g of Lipiodol. Subsequently, the aforementioned Lipiodol and 4.3 g of polylactate were poured into a flask. Moreover, the stir bar of the magnetic stirrer was put into the flask. A nitrogen atmosphere was created inside the flask. The flask was heated by the water bath at 80° C. While the flask was heated, the stir bar was rotated at 50 rpm. As a result, a molten raw material containing the polylactate, Lipiodol, and MIRIPLA was obtained. With the raw material, the embolic material was produced through the same method as in the above-described (3). The produced embolic material contains polylactate, Lipiodol, and MIRIPLA. The produced embolic material will be hereinafter referred to as an embolic material for evaluation.

(6-2) Evaluation Test for Pharmaceutical Drug Time-Release Properties

With regard to the embolic material for evaluation, the pharmaceutical drug time-release properties were evaluated. The method thereof is as follows. First, the mass of the embolic material for evaluation was measured. Then, based on the mass, the mass of Pt contained in the embolic material for evaluation was calculated. Pt is a component of MIRIPLA.

Subsequently, the embolic material for evaluation was immersed in a bottle filled with 10 mL of hydrochloric acid having a concentration of 1 mol/L for 24 hours. Then, the liquid part was taken out from the bottle. The mass of Pt contained in the liquid part was measured by an atomic absorption spectrophotometer. Next, the mass of Pt contained in the liquid part was converted into a value which would be obtained under an assumption that the mass of Pt contained in the embolic material for evaluation is a constant amount. This value will be hereinafter referred to as a cumulative platinum discharge amount.

Figure 4:
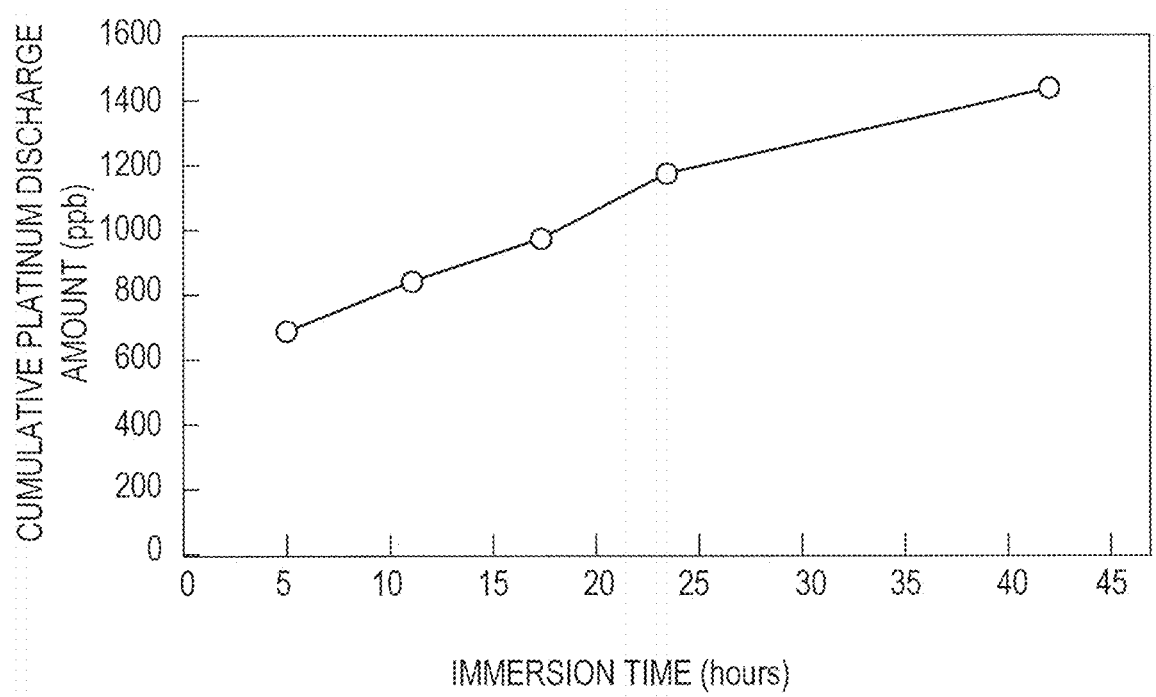
FIG. 4 is a graph showing a relation between an immersion time and a cumulative platinum discharge amount of an embolic material for evaluation.

The above-described process was also performed for each of cases in which the time period for immersing the embolic material for evaluation in the hydrochloric acid was 48 hours, 72 hours, 96 hours, and 168 hours. In FIG. 4, the relation between the immersion time and the cumulative platinum discharge amount is shown. As shown in FIG. 4, the cumulative platinum discharge amount gradually increased as the immersion time became longer. Thus, the embolic material for evaluation has the pharmaceutical drug time-release properties.

Other Embodiments

The embodiments of the present disclosure are described hereinbefore. Nevertheless, the present disclosure is not limited to the above-described embodiments and may be embodied in various forms.

(1) Functions of one component in the aforementioned embodiments may be distributed to two or more components. Functions of two or more components may be achieved by one component. A part of the structures of the aforementioned embodiments may be omitted. At least a part of the structures of the aforementioned embodiments may be added to or replaced with other structures of another one of the aforementioned embodiments. It should be noted that any and all forms that are encompassed in the technical ideas identified by the languages in the claims are embodiments of the present disclosure.

(2) In addition to the above-described embolic material, the present disclosure can be embodied in various forms, such as a product comprising the embolic material as a component and a method for treating humans or animals using the embolic material.

What is claimed is:

1. A method of producing an embolic material comprising:
    preparing a molten raw material by mixing polycaprolactone and a liposoluble contrast medium of ethyl ester of iodinated poppy-seed oil fatty acid at a ratio of one to one in a nitrogen atmosphere at 80° C.;
    extruding the molten raw material, maintained at 80° C., from a tip of an injection cylinder into a pipe filled with warm water at 80° C.; and
    cooling the molten raw material to solidify the molten raw material by sending the molten raw material to a cold water tank reserving cold water at 0° C. through the pipe.

2. The method of producing an embolic material according to claim 1, wherein the liposoluble contrast medium contains a pharmaceutical drug.

3. The method of producing an embolic material according to claim 1, wherein the raw material extruded into the warm water forms spherical shapes in the warm water.

* * * * *